United States Patent [19]

Sleiman

[11] Patent Number: 4,738,659
[45] Date of Patent: Apr. 19, 1988

[54] CATHETER AND ITS METHOD OF USE WITH A CYSTOSCOPIC LENS

[76] Inventor: Raymond A. Sleiman, 3320 Los Coyotes Diagl, Long Beach, Calif. 90808

[21] Appl. No.: 864,532

[22] Filed: May 19, 1986

[51] Int. Cl.$^4$ ............................................. A61M 25/00
[52] U.S. Cl. ............................................ 604/96; 128/4; 604/280
[58] Field of Search ........................................ 128/3–8, 128/21; 604/96–103, 280

[56] References Cited

U.S. PATENT DOCUMENTS

| | | | |
|---|---|---|---|
| 2,548,602 | 4/1951 | Greenburg | 128/4 |
| 3,417,745 | 12/1968 | Sheldon | 128/6 |
| 3,809,072 | 5/1974 | Ersek et al. | 128/6 X |
| 3,913,565 | 10/1975 | Kawahara | 128/8 X |
| 4,148,319 | 4/1979 | Kasper et al. | 604/96 |
| 4,176,662 | 12/1979 | Frazer | 604/21 X |

*Primary Examiner*—Dalton L. Truluck
*Attorney, Agent, or Firm*—Kane, Dalsimer, Sullivan, Kurucz, Levy, Eisele and Richard

[57] ABSTRACT

A direct visualization urethral catheter includes a catheter having a side wall and an open distal end, a proximal end and a bore extending between the ends. In use, the catheter is adapted to be associated with a cystoscope which is placed within the bore of the catheter from the proximal end and has a lens at the distal end for direct vision of the body orifice through the open distal end. The distal end is so constructed and arranged with reinforcing means to permit the catheter lens to be inserted into the selected body orifice while assuring against unintentional penetration of the lens through the open distal end.

26 Claims, 2 Drawing Sheets

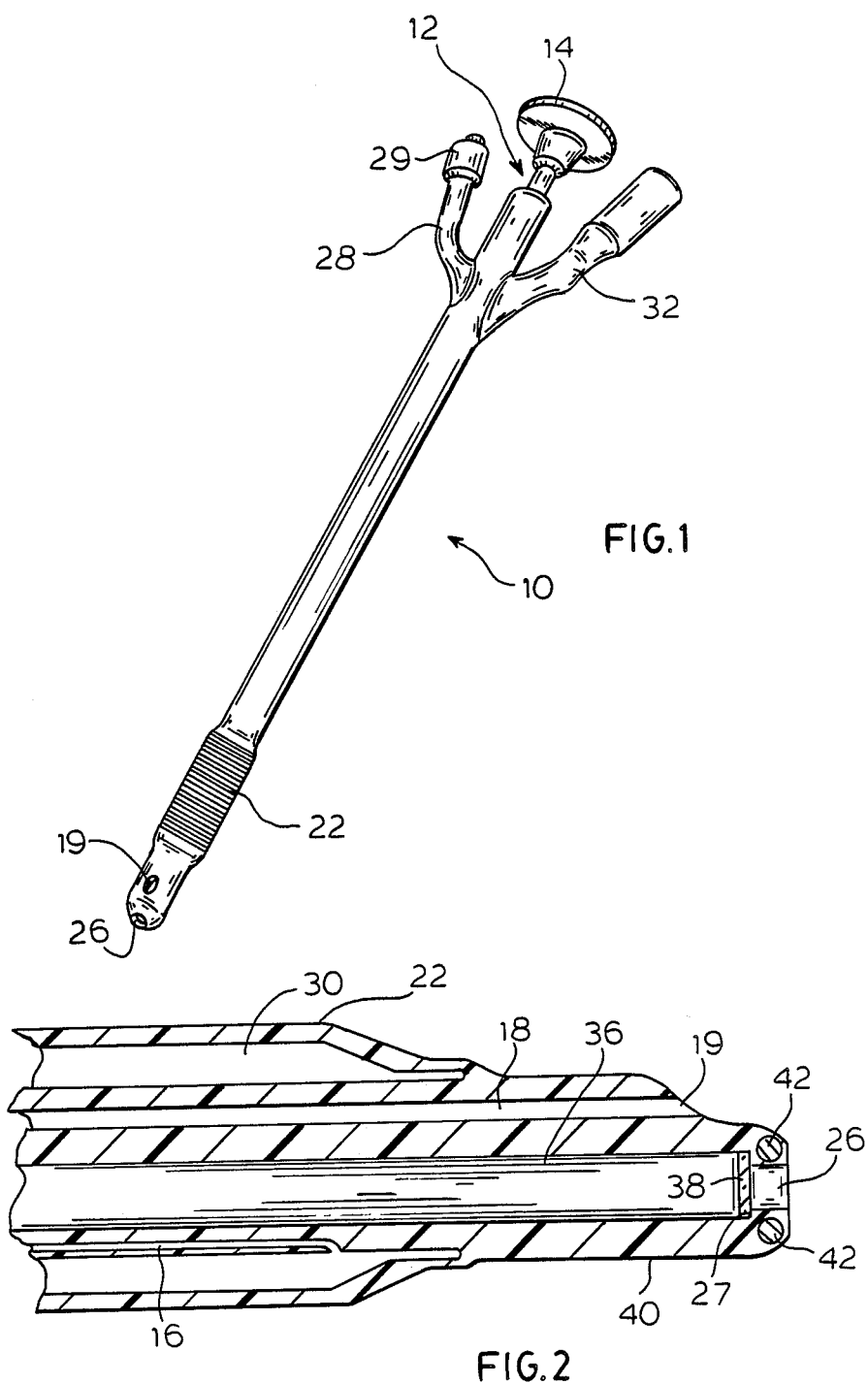

CATHETER AND ITS METHOD OF USE WITH A CYSTOSCOPIC LENS

FIELD OF THE INVENTION

The present invention relates to catheters, and, particularly, catheters capable of receiving a telescopic element with a cystoscopic lens for direct visualization of a body cavity as well as to a method of using a catheter with a cystoscopic lens for such purposes.

BACKGROUND OF THE INVENTION

There is an ever increasing need and demand for direct vision catheterization especially following a transurethral resection of the prostate or following urethral dilation of a stricture. In this regard, it has been determined that these procedures may be facilitated by deploying a cystoscope lens in conjunction with a urethral catheter.

Furthermore, catheters are usually made of an elastomer material, e.g. latex rubber, silicone, and are generally formed by conventional dipping techniques. However, these techniques do not lend themselves to the formation of structure at the catheter tip that, by dipping alone will prevent accidental penetration of the lens system of a cystoscope through an open end of the catheter formed for direct viewing. In this connection, it is extremely detrimental to have the lens system extend through or slide relative to the catheter tip during the insertion procedure which could lead to injury of the patient or the walls of the cavity or neighboring organs or body parts.

SUMMARY OF THE INVENTION

The principal object of the present invention is to provide a catheter having a predetermined length capable of receiving a commercially available telescope and having a reinforced tip to prevent the lens from protruding through the catheter tip during insertion and use within a body cavity.

Another object of the invention is to provide a novel catheter that is shorter than normal in length with a relatively flexible body and rigidified tip that facilitates the performance of a technique utilizing a telescope therewith for direct visualization of a body cavity.

A further object is to provide an elastomeric catheter of the foregoing type capable of being inserted into a body cavity along with the lens system of an internally disposed cystoscope and one that does not slide relative to the lens system during insertion.

Additional objects and advantages of the present invention will become apparent from the following detailed description of the invention which is to be taken in conjunction with the drawings.

BRIEF DESCRIPTION OF THE DRAWINGS

FIG. 1 is a perspective view of a catheter possessing the attributes of the present invention;

FIG. 2 is an enlarged fragmentary sectional view of the distal end of the catheter of FIG. 1;

DETAILED DESCRIPTION OF THE PREFERRED EMBODIMENT

Figure 3:
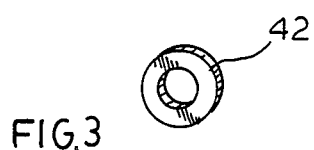
FIG. 3 is a perspective view illustrating an annular ring for reinforcement of the catheter tip.

FIG. 1 illustrates a catheter 10 of the present invention preferably composed of a flexible latex or silicone rubber or other suitable elastomeric material. The catheter 10 contains a central lumen into which a telescope 12 having eyepiece 14 is inserted. At the distal tip of the catheter is viewing aperture 26 as well as the abutment or shoulder 27. The catheter 10 also contains a balloon inflation lumen 16 extending longitudinally therethrough (see FIG. 2). Neck 28 housing part of inflation lumen 16 branches from the proximal end of the catheter and contains an adapter 29 for connection with an inflation means to inflate balloon member 22 in a conventional manner. The balloon member 22 having an inflatable air pocket 30 is adapted to retain the catheter within the preselected body orifice when inflated. (Other catheter retention means may be employed such as mallecot type wings.) A neck 32 housing lumen 18 is contained at the proximal end of the catheter for connection with an irrigation system to provide continuous irrigation of the working area through orifice 19.

A cystoscope 12 having telescope element 36 possesses a cystoscopic lens 38 at a distal end thereof. The telescope element is rigid in structure and is generally composed of stainless steel or the like. The telescope element 36 is placed within the central lumen of the catheter and advanced so that the lens 38 is flush with shoulder 27 and viewing aperture 26.

In order to prevent inadvertent or accidental penetration of the distal end of the telescope element 36 through the aperture 26, catheter tip 40 is suitably rigidified. Towards this end, reinforcing washer or ring 42 may be incorporated at the tip 40 and is preferably a rigid porous material. The porosity of the ring 42 allows the latex of the catheter to bond to the ring during manufacture and the rigidity provides a retention means to help prevent protrusion of the telescope. In this manner, transurethral insertion of the catheter with telescope is accomplished in a safe manner.

Figure 4:
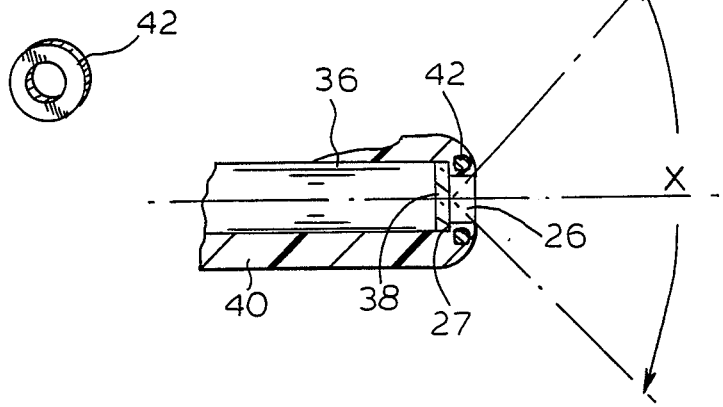
FIG. 4 is a fragmentary longitudinal sectional view of the distal tip of a first embodiment of the catheter of the present invention having the annular ring of FIG. 3 set therein.

FIG. 4 further highlights the wide angle viewing capacity achieved by the distally advanced placement of lens 38 in accordance with the present invention. Telescope element 36 has a greater diameter than viewing aperture 26 so that the edges of the lens or telescope contact the shoulder 27 inside of catheter tip 40. The reinforced distal end tightly embraces the distal end of the telescope element 36 to assure centering of the lens 38 relative to the tip 40. The inner diameter of ring 42 is also less than the outer diameter of lens 38 to assure that the catheter does not slip back over the lens despite forces on the catheter tip during insertion and advancement of the catheter.

Figure 5:
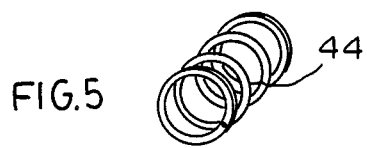
FIGS. 5 and 6, respectively, show a coil and a second embodiment of the catheter of the present invention having the coil set therein for reinforcement of the catheter tip.
Figure 6:
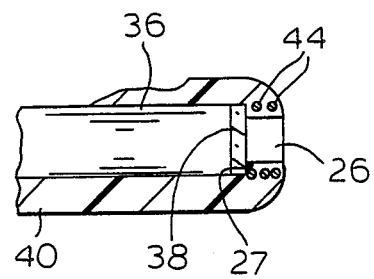

FIG. 5 illustrates a second reinforcement device in the form of a ring, coil or spring 44 that is adapted to be incorporated in the catheter tip 40. Coil 44 may be composed of a metal or a plastic, or it may comprise a non-stretchable thread or strand bonded into the latex as shown in FIG. 6. A single coil or a plurality of coils of the same or different materials may be utilized.

Typically catheters have a working length of 13" and an overall length of 16"–17". The catheter of this invention is shorter and is preferably 10" overall, but may range between 9" and 12" in overall length.

The length of the catheter 10 will vary depending upon the cystoscope 12 being accommodated. Towards this end, a Karl Storz, ACMI, Richard Wolf or Olympus cystoscope to mention a few may be employed. Normally cystoscopes usable with this invention possess lens tubes varying in length from 10" to 12".

While multiport catheters of varying designs are usable with this invention, a three-way catheter is preferred. One port is for the cystoscopic lens system, one port for irrigation, and one port for inflation. In this regard the balloon may range in capacity from 3 to 40 cc. Also at least 24 French size (diameter) is preferred.

Thus the present invention provides viewing angles as large as is possible. This is accomplished by having the distal end of the cystoscopic lens system approach as closely as possible the aperture 26 of associated tip 40 of the catheter. It has been determined that the lens must be as close as possible to the open distal end of the catheter to provide the widest angle of view. This is facilitated by the provision of reinforcement at the tip 40 of the catheter. Without the reinforcement at this location, the deformable catheter tip 40 would easily slide back on the telescopic element 36.

Figure 7:
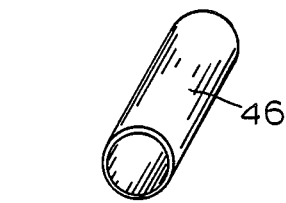
FIGS. 7 and 8, respectively, illustrate a sleeve and a third embodiment of the catheter of the present invention having the sleeve set therein for reinforcement of the catheter tip.
Figure 8:
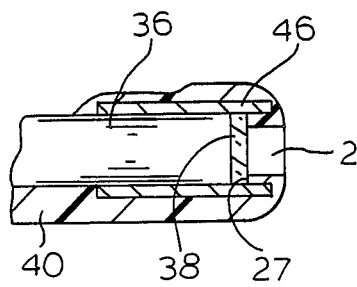

FIG. 7 illustrates a further embodiment of a catheter tip reinforcing device in the form of a sleeve 46. A preferable composition of sleeve 46 is a non stretchable material into which the latex material may penetrate. FIG. 8 illustrates sleeve 46 bonded into catheter tip 40.

Any of the above designs may also have a surface treatment to promote bonding between the catheter material and the reinforcing means.

It will be understood that further structural configurations are within the scope of the present invention. While a detailed description of the invention has been provided, the scope of the invention is not to be limited thereby, but is to be determined by the claims which follow.

What is claimed is:

1. A direct visualization catheter comprising in combination:
    a tubular catheter having a side wall and an open distal end, a proximal end and a bore extending between the ends;
    an inflatable balloon on the exterior of the side wall of the catheter and spaced a short distance from the distal end;
    means for inflating the balloon to an inflated position from a collapsed position to facilitate retention of the catheter within a selected body orifice;
    a fluid passage located on the side wall of the catheter between the balloon and distal end; and
    means for accommodating a separate telescope within the bore of the catheter and a lens thereof at the distal end for direct vision of the body orifice through the open distal end, the telescope being inserted and placed within the bore through the proximal end prior to the insertion of the catheter within the body orifice, the distal end being so constructed and arranged with reinforcing means to rigidify the distal end to permit a lens to be inserted into the body orifice with the catheter while preventing unintentional penetration of the lens through the open distal end and assuring that the catheter distal end does not slip back over the lens despite forces on the catheter distal end during insertion and advancement of the catheter into the body orifice said reinforcing means being located distal of said lens 2. A direct visualization catheter according to claim 1, wherein the balloon inflation means includes a lumen extending from adjacent the proximal end within the catheter wall and into communication with the interior of the balloon and a coupling means at the proximal end for coupling the lumen to a source of pressure for inflating the balloon.

3. A direct visualization catheter according to claim 1, wherein the continuous irrigation means includes a lumen extending from adjacent the proximal end and within the catheter wall and exiting distal of the balloon.

4. A direct visualization catheter according to claim 1, wherein the balloon has 3 to 40 cc capacity.

5. A direct visualization catheter according to claim 1, wherein the catheter is approximately between 9"–12" in length to accommodate a cystoscopic lens.

6. The invention in accordance with claim 1, wherein the bore has a reduced diameter distal end is so constructed and arranged to provide an abutment to the lens which is of greater diameter than the bore at the reduced diameter distal end such that the bore is as close to the opening of the distal end as possibe to permit the widest angle of view of the body orifice through the open distal end.

7. The invention in accordance with claim 1, wherein the reinforcing means is a non-stretchable material.

8. The invention in accordance with claim 1, wherein the reinforcing means is non-stretchable thread.

9. The invention in accordance with claim 1, wherein the reinforcing means is a coil spring.

10. The invention in accordance with claim 1, wherein the reinforcing means is a porous annular ring.

11. A direct visualization urethral catheter comprising in combination:
    a tubular catheter having a side wall and an open distal end, a proximal end and a bore extending between the ends;
    a separate telescopic member extending within the bore of the catheter from the proximal end and having a lens at the distal end for direct vision of the body orifice through the open distal end, the telescope being inserted and placed within the bore through the proximal end prior to the insertion of the catheter within the body orifice; and
    the distal end being so constructed and arranged with reinforcing means to rigidify the distal end to permit the lens to be inserted into the body orifice with the catheter while preventing unintentional penetration of the lens through the open distal end and assuring that the catheter distal end does not slip back on the lens despite forces on the catheter distal end during insertion and advancement of the catheter into the body orifice said reinforcing means being located distal of said lens.

12. The invention in accordance with claim 11, wherein the bore has a reduced diameter distal end is so constructed and arranged to provide an abutment to the lens which is of greater diameter than the bore at the reduced diameter distal end such that the bore is as close to the opening of the distal end as possible to permit the widest angle of view of the body orifice through the open distal end.

13. The invention in accordance with claim 11, wherein the reinforcing means is a non-stretchable material.

14. The invention in accordance with claim 11, wherein the reinforcing means is non-stretchable thread.

15. The invention in accordance with claim 11, wherein a retention means is on the exterior of the side wall of the catheter and is spaced a short distance from the distal end.

16. The invention in accordance with claim 11, wherein the reinforcing means is a coil spring.

17. The invention in accordance with claim 11, wherein the reinforcing means is a porous annular ring.

18. A method of direct visualization of a selected body orifice comprising the steps of:
providing a catheter having an open distal end, a proximal end and a bore extending between the ends;
providing a separate cystoscope having a telescopic element and a lens at the distal end;
inserting the telescopic element into the bore of the catheter through the proximal end prior to the insertion of the catheter within the body orifice;
locating the lens as close to the open distal end as possible to permit the widest angle of view of the body orifice through the open distal end; and inserting the catheter with located lens into the selected body orifice for viewing of the body orifice; and
providing the catheter distal end with an abutment for the lens and rigidifying means to assure against unintentional penetration of the lens through the open distal end of the catheter during insertion and use within the body orifice and assuring that the catheter distal end does not slip back on the lens despite forces on the catheter distal end during insertion and advancement of the catheter into the body orifice said reinforcing means being located distal of said lens.

19. The method of claim 18 including the step of deploying retention means for facilitating the retention of the catheter within the body orifice.

20. The method of claim 19 wherein the retention means is an inflatable balloon inflating the balloon after insertion of the catheter with lens into the body orifice.

21. The method of claim 18 including the step of:
irrigating the body orifice during or following insertion of the catheter with lens into the body orifice.

22. A direct visualization catheter comprising in combination:
a tubular catheter having a side wall and an open distal end, a proximal end and a bore extending between the ends;
an inflatable balloon on the exterior of the side wall of the catheter and spaced a short distance from the distal end;
means for inflating the balloon to an inflated position form a collapsed position to facilitate retention of the catheter within a selected body orifice;
a fluid passage located on the side wall of the catheter between the balloon and distal end; and
means for accommodating a telescope within the bore of the catheter and a lens thereof at the distal end for direct vision of the body orifice through the open distal end wherein the distal end is so constructed and arranged with reinforcing means to permit a lens to be inserted into the body orifice with the catheter while preventing unintentional penetration of the lens through the open distal end, said reinforcing means comprising a coil spring surrounding said bore at said distal end, said bore being constructed to have a reduced diameter at said distal end wherein said coil spring is located.

23. The invention in accordance with claim 22 wherein the bore at the reduced diameter distal end is so constructed and arranged to provide an abutment to the lens which is of greater diameter than the bore at the reduced diameter distal end such that the bore is as close to the distal end as possible to permit the widest angle of view of the body orifice through the open distal end.

24. A direct visualization urethral catheter comprising in combination:
a tubular catheter having a side wall and an open distal end, a proximal end and a bore extending between the ends;
a telescopic member extending within the bore of the catheter from the proximal end and having lens at the distal end of said catheter for direct vision of the body orifice through the open distal end; and
the distal end being so constructed and arranged with reinforcing means to permit the lens to be inserted into the body orifice with the catheter while preventing unintentional penetration of the lens through the open distal end said reinforcing means comprising one or more coils of a coil spring surrounding said bore at said distal end, said bore being constructed to have a reduced diameter at said distal end wherein said coil spring is located.

25. The invention in accordance with claim 24 wherein the bore at the reduced diameter distal end is so constructed and arranged to provide an abutment to the lens which is of greater diameter than the bore at the reduced diameter distal end so that the bore is as close to the distal end as possible to permit the widest angle of view of the body orifice through the open distal end.

26. A method of direct visualizaiton of a selected body orifice comprising the steps of:
providing a catheter having an open distal end, a proximal end and a bore extending between the ends;
providing a cystoscope having a telescopic element and a lens at the distal end of said catheter;
inserting the telecopic element into the bore of the catheter through the proximal end;
locating the lens as close to the open distal end as possible to permit the widest angle of view of the body orifice through the open distal end; and inserting the catheter with located lens into the selected body orifice for viewing of the body orifice providing the catheter distal end with an abutment for the lens and rigidifying means to assure against unintentional penetration of the lens through the open distal end of the catheter during insertion and use within the body orifice and bore being constructed to have a reduced diameter at said distal end wherein said rigidifying means comprising one or more coils of a coil spring is located.

* * * * *